United States Patent [19]

Nightingale

[11] Patent Number: 4,893,919
[45] Date of Patent: Jan. 16, 1990

[54] HEAD SUPPORTED OPTICAL SUSPENSION SYSTEM

[76] Inventor: Edmund Nightingale, 3314 Steuben Ave., Bronx, N.Y. 10467

[21] Appl. No.: 184,188

[22] Filed: Apr. 21, 1988

[51] Int. Cl.⁴ .......................... A61B 3/10; G02C 1/00
[52] U.S. Cl. .................................... 351/205; 351/158; 350/145
[58] Field of Search ................ 351/205, 156, 157, 41, 351/158; 350/145, 146

[56] References Cited
U.S. PATENT DOCUMENTS
2,935,910  5/1960  Schmidt ..................... 351/156 X Primary Examiner—Rodney B. Bovernick
Attorney, Agent, or Firm—Michael I. Kroll

[57] ABSTRACT

A head supported optical suspension system is provided and consists of an optical device carried in a support frame assembly attached to a suspension unit which is dependent on each side of a headband worn on a head of a person so that hands of the person are free to do other work and in addition, the elimination of hand tremors, which are subject to great magnification by the optical device.

22 Claims, 2 Drawing Sheets

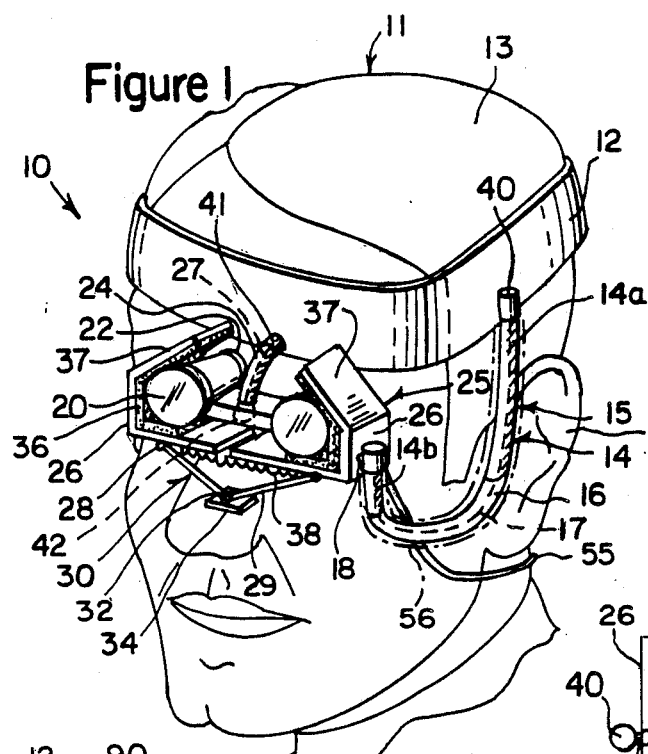
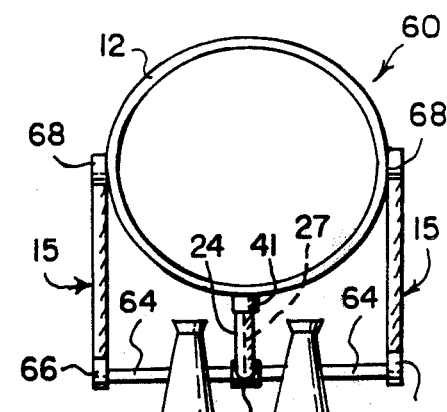
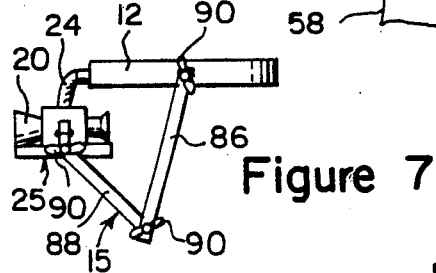
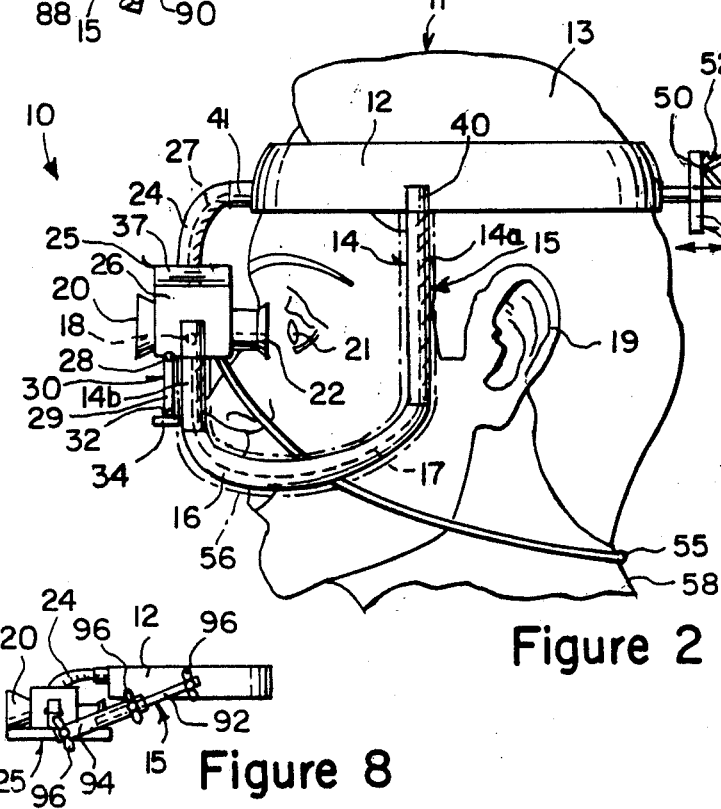
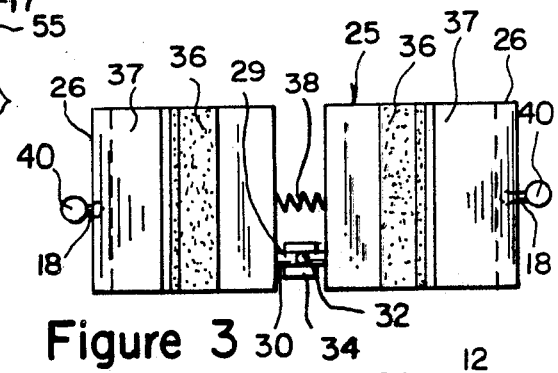
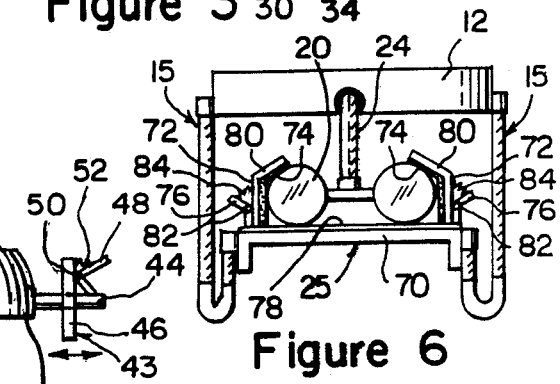
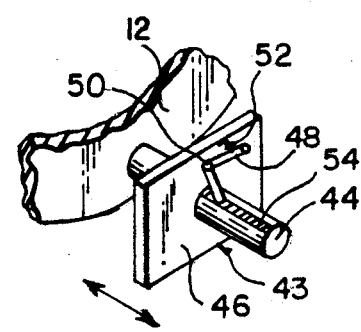
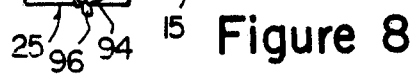

4,893,919

HEAD SUPPORTED OPTICAL SUSPENSION SYSTEM

BACKGROUND OF THE INVENTION

1. Field of the Invention

The instant invention relates generally to optical apparatuses and more specifically it relates to a head supported optical suspension system.

2. Description of the Prior Art

Numerous optical apparatuses have been provided in prior art that are adapted to be worn on the heads of people. While these units may be suitable for the particular purpose to which they address, they would not be as suitable for the purposes of the present invention as heretofore described.

SUMMARY OF THE INVENTION

A primary object of the present invention is to provide a head supported optical suspension system that will overcome the shortcomings of the prior art devices.

Another object is to provide a head supported optical suspension system that is worn by a person thereby eliminating the need to hold an optical device with the hands, which are thus freed to do other work.

Another object is to provide a head supported optical suspension system that will eliminate all hand tremors, which are magnified by the power of the optical device.

An additional object is to provide a head supported optical suspension system that is adaptable to hold various types of optical devices within its suspension system.

A further object is to provide a head supported optical suspension system that is simple and easy to use.

A still further object is to provide a head supported optical suspension system device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of a person wearing the present invention.

FIG. 2 is a side view of the person wearing the present invention.

FIG. 3 is a top view of the support frame assembly.

FIG. 4 is a partial perspective view of the headband with the adjustable weight assembly at the rear thereof.

FIG. 5 is a top view of a first modification in which the support frame assembly is eliminated by utilizing a modified optical device.

FIG. 6 is a front view of a second modification in which a second type of support frame assembly is utilized.

FIG. 7 is a left side view of a third modification in which a second type of suspension unit is utilized.

FIG. 8 is a left side view of a fourth modification in which a third type of suspension unit is utilized.

DETAILED DESCRIPTION OF THE PREFERRED EMBODIMENTS

Figure 9:
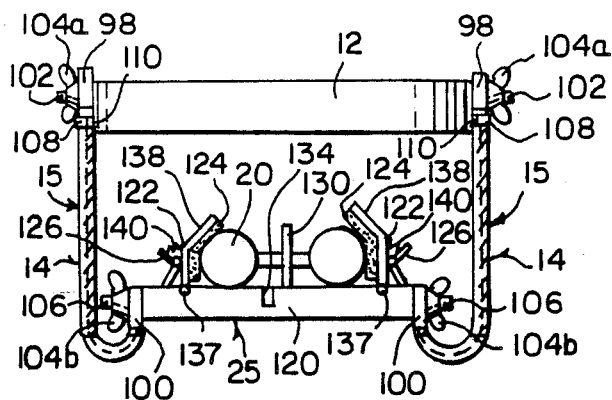
FIG. 9 is a front view of a fifth modification in which a fourth type of suspension unit and a third type of support frame assembly is utilized.
Figure 11:
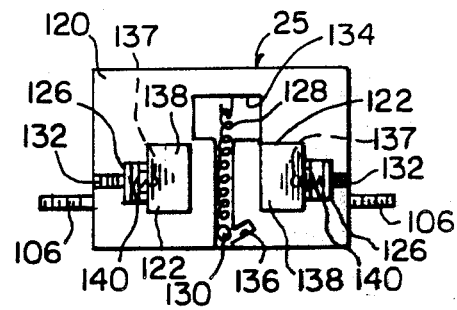
FIG. 11 is a top view of the third type of support frame assembly.

Turning now descriptively to the drawings, in which similar reference characters denote similar elements throughout the several views, FIGS. 1 and 2 illustrate a head support optical suspension system 10 consisting of an endless annular headband 12 for engaging around head 13 of a person 11 above ears 19. A suspension unit 15 is dependent on each side of the headband 12 substantially extending downward and forward the ears 19 of the person 11. A support frame assembly 25 is attached to the suspension unit 15 so that the support frame assembly 25 is adjacent eyes 21 of the person 11. An optical device 20, such as a pair of binoculars, is carried in the support frame assembly 25. The optical device 20 includes eyepieces 22 to be placed close to the eyes 21 of the person 11 for viewing therethrough, so that hands (not shown) of the person 11 are free to do other work and all hand tremors, which are magnified by the optical power of said optical device are eliminated.

The optical suspension system 10 further contains a connector 41 attached to front of the headband 12. A front flexible tube 24 is attached at one end to the front connector 41. A ball joint connector 42 is attached to the front flexible tube 24 and contacts center of the optical device 20, while a plurality of stiffening rods 27 extend through the front flexible tube 24 so that the optical device 20 can further be supported and adjusted therefrom.

The suspension unit 15 consists of a pair of quick-release connectors 40, a pair of U-shaped flexible tubes 14 and a pair of friction-loaded pivot pins 18. Each of the quick-release connectors 40 is attached to an opposite side of the headband 12, while each of the tubes 14 is attached at one end to one of the connectors 40. Each of the friction-loaded pivot pins 18 is attached between other end of one of the tubes 14 and the support frame assembly 25 so that the support frame assembly can be properly positioned adjacent the eyes 21 of the person.

Each of the U-shaped flexible tubes 14 consists of a long generally straight flexible tube segment 14a attached at one end to one of the quick-release connectors 40. A short generally straight flexible tube segment 14b is attached at one end to one of the pivot pins 18 while a U-shaped tube fitting 16 is attached between the long tube segment 14a and the short tube segment 14b. A plurality of stiffening rods 17 extend through the long tube segment 14a, the U-shaped tube fitting 16 and the short tube segment 14b. A protective sleeve 56, shown in phantom, can be used to cover the long tube segment 14a, the U-shaped tube fitting 16 and the short tube segment 14b.

The support frame assembly 25 as shown in FIGS. 1, 2 and 3, consists of a pair of platforms 26, each of which includes an oblique angle top hold down arm segment 37. A pair of padding members 36 are provided in which each is shaped like one of the platforms 26 and fits into each of the platforms to cushion the optical device 20. A spring 38 is connected to underside and between each of the platforms 26 to urge the platforms together to hold the optical device 20 therebetween.

A platform widener 30 is provided and consists of a pair of pivot pins 28, each mounted to the underside of each of the platforms 26. A pair of arms 29 are each connected at one end to one of the pivot pins 28, while a swivel joint 32 is attached to the other ends of both of the arm 29. A push plate 34 is attached to the swivel joint 32 so that if the push plate 34 is pressed upwardly the platforms 26 will move apart allowing the optical device 20 to be installed and removed.

As best seen in FIGS. 2 and 4 an adjustable weight assembly 43 is provided to equalize weight distribution of the optical device 20 in front of the headband 12. The adjustable weight assembly 43 consists of a rod 44 extending rearwardly from back of the headband 12 with rod 44 having a top scored surface 54 thereon so that an adjustable weight 46 can slideably fit onto the rod 44. A V-shaped friction lock lever 48 is pivotly mounted at 50 to back of the adjustable weight 46 above the scored surface 54 of the rod 44. An expansion spring 52 is mounted between the back of the adjustable weight 46 and the friction lock lever 48 to bias the friction lock lever against the scored surface 54 of the rod 44.

A security cord 55 is attached at each end to a corner of each of the platforms 26. The security cord 55 extends around neck 58 of the person 11 so that when the headband 12 is removed from the head 13 of the person 11, or the suspension unit 15 is disconnected from the headband 12 by release of the connectors 40, the security cord 55 will hold the suspension unit 15 to the person 11.

A modified head supported optical suspension system 60 is shown in FIG. 5 in which the support frame assembly 25 can be eliminated and a modified optical device 62 can be substituted in its place. The suspension unit 15 remains the same but the modified optical device 62 has an integral extension rod 64 at each side. The purpose of the rods 64 are to engage with the suspension unit 15. The fittings of the modified optical device 62 to the suspension unit 15 are through special ball-lock quick release fittings 66 whose engagement results in the modified optical device 62 being held in a horizontal position. The fittings 68 of the suspension unit 15 to the headband 12 are similar to the fittings 66 on the modified optical device 62, except that here the suspension unit 15 rests in a vertical position. These latter fittings 68 also enables the person 11 to flip the modified optical device 62 upwards when not needed, by simple pressure on the ball-lock fittings 68.

It is the configuration of the fittings 66 and 68 that result in the modified optical device 62 being held in a horizontal position and the suspension unit 15 being held vertically from the headband 12. The friction-loaded swivel fittings 66 aids in adjusting the modified optical device 62 to the eyes 21 of the person 11. The ball-lock fittings 68 at the headband 12 enables the person 11 to flip the suspension unit 15 with the modified optical device 62 upwards when not needed.

The attachment fittings 66 between the suspension unit 15 and the modified optical device 62 may be of the snap-in types; however, friction-loaded swivels or pivots should be included to afford proper adjustment of the modified optical device 62, to the eyes 21 of the person 11. The attachment fittings 68 between the suspension unit 15 and the headband 12 may also be of the snap-in types; however, in this case, provision is made so that the suspension unit 15 with the modified optical device 62 may be flipped up and out of the way when not wanted. The attachment fittings 66 and 68 are cylindrical with planar surfaces so in this way the modified optical device 62 is maintained horizontally, while the suspension unit 15 is maintained vertically from the headband 12.

FIG. 6 shows the support frame assembly 25 being of a second type consisting of a platform 70, a pair of sliding bars 72, a pair of padding members 74 and a pair of friction lock levers 76. The platform 70 has a scored track 78 extending across top surface thereof. Each of the sliding bars 72 travels within the track 78 and includes a oblique angle top hold down arm segment 80. Each of the padding members 74 is shaped like one of the sliding bars 72 and fits into one of the sliding bars to cushion the optical device 20. Each of the friction lock levers 76 is pivotly mounted at 82 to one of the sliding bars 72 and is spring loaded thereto at 84 so as to retain the optical device 20 on the platform 70 when the lever 76 is released thereby engaging with the scored track 78 on the platform 70.

FIG. 7 shows the suspension unit 15 being of a second type consisting of a pair of upper arms 86, a pair of lower arms 88 and wing nuts 90. Each of the upper arms 86 is pivotly attached to an opposite side of the headband 12. Each of the lower arms 88 is pivotly attached to one of the upper arms 86 and the support frame assembly 25 so that the support frame assembly can be properly positioned adjacent the eyes 21 of the person 11. The wing nuts 90 are for locking the upper arms 86 and the lower arms 88 in the proper position. Each of the wing nuts 90 is located at one of the pivotly attached ends of the upper arms 86 and the lower arms 88.

FIG. 8 shows the suspension unit 15 being of a third type consisting of a pair of upper arms 92, a pair of lower arms 94 and wing units 96. Each of the upper arms 92 is pivotly attached to an opposite side of the headband 12. Each of the lower arms 94 is telescopically attached to one of the upper arms 92 and pivotly attached to the support frame assembly 25 so that the support frame assembly 25 can be properly positioned adjacent the eyes 21 of the person 11. The wing nuts 96 are for locking the upper arms. The wing nuts 96 are for locking the upper arms 92 and the lower arms 94 in the proper position. Four of the wing nuts 96 are located at the pivotly attached ends of the upper arms 92 and the lower arms 94 while two others are at the telescopically attached ends of the upper arms 92 and the lower arms 94.

Figure 10:
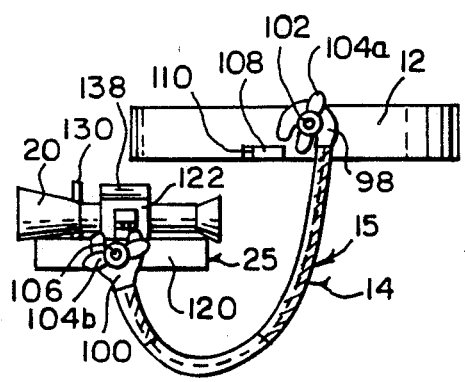
FIG. 10 is a left side view of the fifth modification thereof.

FIGS. 9 and 10 show the suspension unit 15 being of a fourth type which is similar to the suspension unit 15 shown in FIGS. 1 and 2. The pair of quick-release connectors 40 are eliminated and replaced by a pair of U-shaped fittings 98 while the pair of friction-loaded pivot pins 18 are eliminated and replaced by a pair of Y-shaped fittings 100. The structure of the pair of U-shaped flexible tubes 14 remain the same and are retained. Each of the U-shaped fittings 98 is pivotly attached to an opposite side of the headband 12 while each of the Y-shaped fittings 100 is pivotly attached to an opposite side of the support frame assembly 25 so that the support frame assembly 25 can be properly positioned adjacent the eyes 21 of the person 11.

A first pair of threaded shafts 102 are each attached to an opposite side of the headband 12 so that wing nuts 104a can be threaded onto the threaded shafts 102 for locking the U-shaped fittings 98 to the headband 12. A second pair of threaded shafts 106 are each attached to an opposite side of the support frame assembly 25 so that wing nuts 104b can be threaded onto the threaded shafts 106 for locking the Y-shaped fittings 100 to the support frame assembly 25 to keep the support frame assembly in the proper position.

A pair of stop bars 108 are also provided in which each is hingably attached at one end 110, parallel to an opposite side of the headband 12 so that free end can be moved towards and away from the headband 12. When the free ends of the stop bars 108 are moved towards the headband 12 the stop bars 108 will contact distal ends of the U-shaped fittings 98 thus holding the support frame assembly 25 with the optical device 20 at eye level. When the free ends of the stop bars 108 are moved away from the headband 12 and the first pair of wing nuts 104a are loosened, the support frame assembly 25 will move downwardly by pull of gravity out of the way against chest (not shown) of the person 11.

Figure 12:
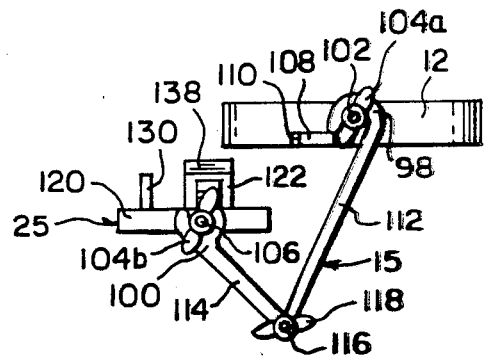
FIG. 12 is a left side view of a sixth modification in which a fifth type of suspension unit is utilized.

FIG. 12 shows the suspension unit 15 being of a fifth type which is similar to the suspension unit 15 shown in FIGS. 9 and 10. The U-shaped flexible tubes 14 are eliminated and replaced by a pair of upper arms 112 and a pair of lower arms 114, which are pivotly attached at 116 to the upper arms 112. Wing nuts 118 are located at the pivotly attached ends of pivot 116 of the upper arms 112 and the lower arms 114 for locking the upper arms 112 to the respective lower arms 114.

FIGS. 9 through 12 show the support frame assembly 25 being of a third type consisting of a platform 120, a pair of sliding bars 112, a pair of padding members 124, a pair of friction lock levers 126, a spring 128 and a vertical rod 130. The platform 120 has two scored tracks 132 spaced apart across top surface thereof, a transverse groove 134 therebetween and an angular niche 136 located at front of the groove 134. Each of the sliding bars 122 pivots at 137 and travels within one of the tracks 132 and includes an oblique angle top hold down arm segment 138. Each of the padding members 124 is shaped like one of the sliding bars 122 and fits into one of the sliding bars to cushion the optical device 20. Each of the friction lock levers 126 is pivotly mounted to one of the sliding bars 122 and is spring loaded thereto at 140 so as to retain the optical device 20 on the platform 120 when the levers 126 are released thereby engaging with the scored tracks 132 on the platform 120. The expansion spring 128 is disposed within the groove 134 and is affixed at one end to the platform 120 at rear of the groove 134. The vertical rod 130 is affixed to other end of the expansion spring 128 and is positioned within the niche 136. When the vertical rod 30 is removed from the niche 136 the rod will contact front center of the optical device 20 to further retain the optical device on the platform 120.

LIST OF REFERENCE NUMBERS 10 head support optical suspension system
11 person
12 endless annular headband
13 head
14 U-shaped flexible tube
14a long generally straight flexible tube segment
14b short generally straight flexible tube segment
15 suspension unit
16 U-shaped fitting
17 stiffening rod
18 friction-loaded pivot pin
19 ear
20 optical device
21 eyes
22 eye piece
24 front flexible tube
25 support frame assembly
26 platform
27 stiffening rod
28 pivot pin
29 arm
30 platform widener
32 swivel joint
34 push plate
36 padding member
37 oblique angle top hold down arm segment
38 spring
40 quick-release connector
41 connector
42 ball joint connector
43 adjustable weight assembly
44 rod
46 adjustable weight
48 V-shaped friction lock lever
50 pivotly mounted
52 expansion spring
54 top scored surface
55 security cord
56 protective sleeve
58 neck
60 modified head supported optical suspension system
62 modified optical device
64 integral extension rod
66 special ball-lock quick release fitting
68 ball lock fitting
70 platform
72 sliding bar
74 padding member
76 friction lock lever
78 scored track
80 oblique angle top hold down arm segment
82 pivotly mounted
84 spring
86 upper arm
88 lower arm
90 wing nut
92 upper arm
94 lower arm
96 wing nut
98 U-shaped fitting
100 Y-shaped fitting
102 first threaded shaft
104a wing nut
104b wing nut
106 second threaded shaft
108 stop bar
110 hinge
112 upper arm
114 lower arm
116 pivot
118 wing nut
120 platform
122 sliding bar
124 padding member
126 friction lock lever
128 expansion spring
130 vertical rod
132 scored track
134 transverse groove
136 angular niche 137 pivot
138 oblique angle top hold down arm segment
140 spring It will be understood that each of the elements described above, or two or more together, may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

1. A head supported optical suspension system which comprises:
   (a) an endless annular headband for engaging around head of a person above ears;
   (b) a suspension unit dependent on each side of said headband substantially extending downward and forward the ears of the person;
   (c) a support frame assembly attached to said suspension unit so that said support frame assembly is adjacent eyes of the person; and
   (d) an optical device carried in said support frame assembly, said optical device includes eyepieces to be placed close to the eyes of the person for viewing therethrough, so that hands of the person are free to do other work and all hand tremors, which are magnified by the optical power of said optical device are eliminated, said optical device further comprising a first connector attached to front of said headband, a front flexible tube attached at one end to said front connector, a second connector attached to said front flexible tube and contacts center of said optical device, a plurality of stiffening rods extending through said front flexible tube so that said optical device can further be supported and adjusted therefrom.

2. A head supported optical device as recited in claim 1, wherein said suspension unit comprises:
   (a) a pair of quick-release connectors, each of which is attached to an opposite side of said headband;
   (b) a pair of U-shaped flexible tubes, each of which is attached at one end to one of said quick-release connectors; and
   (c) a pair of friction-loaded pivot pins, each of which is attached between other end of one of said tubes and said support frame assembly so that said support frame assembly can be properly positioned adjacent the eyes of the person.

3. A head supported optical suspension system as recited in claim 2, wherein each of said U-shaped flexible tubes comprises:
   (a) a long generally straight flexible tube segment attached at one end to one of said quick-release connectors;
   (b) a short generally straight flexible tube segment attached at one end to one of said pivot pins;
   (c) a U-shaped tube fitting attached between said long tube segment and said short tube segment;
   (d) a plurality of stiffening rods extending through said long tube segment, said U-shaped tube fitting and said short tube segment; and
   (e) a protective sleeve to cover said long tube segment, said U-shaped tube fitting and said short tube segment.

4. A head supported optical suspension system as recited in claim 3, wherein said support frame assembly comprises:
   (a) a pair of platforms, each of which includes an oblique angle top hold down arm segment;
   (b) a pair of padding members, each of which is shaped like one of said platforms and fits into each of said platforms to cushion said optical device; and
   (c) a spring connected to underside and between each of said platforms to urge said platforms together to hold said optical device therebetween.

5. A head supported optical suspension system as recited in claim 4, further including a platform widener which comprises:
   (a) a pair of pivot pins, each mounted to the underside of each of said platforms;
   (b) a pair of arms, each connected at one end to one of the pivot pins;
   (c) a swivel joint attached to other ends of both of said arms; and
   (d) a push plate attached to said swivel joint so that if said push plate is pressed upwardly said platforms will move apart allowing said optical device to be installed and removed.

6. A head supported optical suspension system as recited in claim 5, further including an adjustable weight assembly to equalize weight distribution of said optical device in front of said headband, said adjustable weight assembly comprising:
   (a) a rod extending rearwardly from back of said headband, said rod having a top scored surface thereon;
   (b) an adjustable weight to slideably fit onto said rod;
   (c) a V-shaped friction lock lever pivotly mounted to back of said adjustable weight above the scored surface of said rod; and
   (d) an expansion spring mounted between the back of said adjustable weight and said friction lock lever to bias said friction lock lever against the scored surface of said rod.

7. A head supported optical suspension system as recited in claim 6, further comprising a security cord attached at each end to a corner of each of said platforms, said security cord extends around neck of the person so that in one instance when said headband is removed from the head of the person and in another instance when said suspension unit is disconnected from said headband by release of said connectors, said security cord will hold said suspension unit to the person.

8. A head supported optical suspension system as recited in claim 3, wherein said support frame assembly comprises:
   (a) a platform having a scored track extending across top surface thereof;
   (b) a pair of sliding bars, each of which travels within the track and includes an oblique angle top hold down arm segment;

(c) a pair of padding members, each of which is shaped like one of said sliding bars and fits into one of said sliding bars to cushion said optical device; and (d) a pair of friction lock levers, each of which is pivotly mounted to one of said sliding bars and spring loaded thereto so as to retain said optical device on said platform when said lever is released thereby engaging with the scored track on said platform.

9. A head supported optical device as recited in claim 1, wherein said suspension unit comprises:
(a) a pair of upper arms, each of which is pivotly attached to an opposite side of said headband;
(b) a pair of lower arms, each of which is pivotly attached to one of said upper arms and said support frame assembly so that said support frame assembly can be properly positioned adjacent the eyes of the person; and
(c) means for locking said upper arms and said lower arms in the proper position.

10. A head supported optical device as recited in claim 9, wherein said locking means includes a plurality of wing nuts, each of which is located at one of the pivotly attached ends of said upper arms and said lower arms.

11. A head supported optical device as recited in claim 1, wherein said suspension unit comprises:
(a) a pair of upper arms, each of which is pivotly attached to an opposite side of said headband;
(b) a pair of lower arms, each of which is telescopically attached to one of said upper arms and pivotly attached to said support frame assembly so that said support frame assembly can be properly positioned adjacent the eyes of the person; and
(c) means for locking said upper arms and said lower arms in the proper position.

12. A head supported optical device as recited in claim 11, wherein said locking means includes a plurality of wing nuts, some of which are located at the pivotly attached ends of said upper arms and said lower arms and others at the telescopically attached ends of said upper arms and said lower arms.

13. A head supported optical device as recited in claim 1, wherein said suspension unit comprises:
(a) a pair of U-shaped fittings, each of which is pivotly attached to an opposite side of said headband;
(b) a pair of U-shaped flexible tubes, each of which is attached at upper end to one of said U-shaped fittings;
(c) a pair of Y-shaped fittings, each of which is attached to lower end of one of said U-shaped tubes and is pivotly attached to an opposite side of said support frame assembly so that said support frame assembly can be properly positioned adjacent the eyes of the person;
(d) means for locking said U-shaped fittings to said headband; and
(e) means for locking said Y-shaped fittings to said support frame assembly to keep said support frame assembly in the proper position.

14. A head supported optical device as recited in claim 13 wherein said U-shaped fitting locking means includes:
(a) a first pair of threaded shafts, each of which is attached to an opposite side of said headband; and
(b) a first pair of wing nuts, each of which is threadable onto one of said first pair of threaded shafts.

15. A head supported optical device as recited in claim 14, wherein said Y-shaped fitting locking means includes:
(a) a second pair of threaded shafts, each of which is attached to an opposite side of said support frame assembly; and
(b) a second pair of wing nuts, each of which is threadable onto one of said second pair of threaded shafts.

16. A head supported optical device as recited in claim 15, wherein each of said U-shaped flexible tubes comprises:
(a) a long generally straight flexible tube segment attached at one end to one of said U-shaped fittings;
(b) a short generally straight flexible tube segment attached at one end to one of said Y-shaped fittings;
(c) a U-shaped tube fitting attached between said long tube segment and said short tube segment; and
(d) a plurality of stiffening rods extending through said long tube segment, said U-shaped tube fitting and said short tube segment.

17. A head supported optical device as recited in claim 16, further comprising a pair of stop bars each of which is hingeably attached at one end, parallel to an opposite side of said headband so that free end can be moved towards and away from said headband, whereby when the free ends of said stop bars are moved towards said headband said stop bars will contact distal ends of said U-shaped fittings thus holding said support frame assembly with said optical device at eye level and when the free ends of said stop bars are moved away from said headband and said first pair of wing nuts are loosened, said support frame assembly will move downwardly by pull of gravity out of the way against chest of the person.

18. A head supported optical suspension system as recited in claim 17, wherein said support frame assembly comprises:
(a) a platform having two scored track spaced apart across top surface thereof, a transverse groove therebetween and an angular niche located at front of the groove;
(b) a pair of sliding bars, each of which pivots and travels within one of the tracks and includes an oblique angle top hold down arm segment;
(c) a pair of padding members, each of which is shaped like one of said sliding bars and fits into one of said sliding bars to cushion said optical device;
(d) a pair of friction lock levers, each of which is pivotly mounted to one of said sliding bars and spring loaded thereto so as to retain said optical device on said platform when said levers are released thereby engaging with the scored tracks on said platform;
(e) an expansion spring disposed within the groove and affixed at one end to said platform at rear of the groove; and
(f) a vertical rod affixed to other end of said expansion spring and positioned within the niche so that when removed from the niche said rod will contact front center of said optical device to further retain said optical device on said platform.

19. A head supported optical device as recited in claim 1, wherein said suspension unit comprises:
(a) a pair of U-shaped fittings, each of which is pivotly attached to an opposite side of said headband;
(b) a pair of upper arms, each of which is attached at upper end to one of said U-shaped fittings;

(c) a pair of lower arms, each of which is pivotly attached to one of said upper arms;

(d) means for locking each of said upper arms to one of said respective lower arms;

(e) a pair of Y-shaped fittings, each of which is attached to lower end of one of said upper arms and is pivotly attached to an opposite side of said support frame assembly so that said support frame assembly can be properly positioned adjacent the eyes of the person;

(f) means for locking said U-shaped fittings to said headband; and (g) means for locking said Y-shaped fittings to said support frame assembly to keep said support frame assembly in the proper position.

20. A head supported optical device as recited in claim 19, wherein each of said upper arm to lower arm locking means includes a wing nut located at the pivotly attached ends of said upper arm and said lower arm.

21. A head supported optical device as recited in claim 20, wherein said U-shaped fitting locking means includes:

(a) a first pair of threaded shafts, each of which is attached to an opposite side of said headband; and (b) a first pair of wing nuts, each of which is threadable onto one of said first pair of threaded shafts.

22. A head supported optical device as recited in claim 21, wherein said Y-shaped fitting locking means includes:

(a) a second pair of threaded shafts, each of which is attached to an opposite side of said support frame assembly; and (b) a second pair of wing nuts, each of which is threadable onto one of said second pair of threaded shafts.

* * * * *